US012648989B2

(12) United States Patent
Zhang et al.

(10) Patent No.: US 12,648,989 B2
(45) Date of Patent: Jun. 9, 2026

(54) RECOMBINANT BCG, PREPARATION METHOD THEREFOR AND APPLICATION THEREOF

(71) Applicant: XUZHOU HAIRUN BIOTECHNOLOGY CO., LTD., Xuzhou (CN)

(72) Inventors: Yang Zhang, Zhumadian (CN); Pengjv Li, Xuzhou (CN)

(73) Assignee: XUZHOU HAIRUN BIOTECHNOLOGY CO., LTD., Xuzhou (CN)

( * ) Notice: Subject to any disclaimer, the term of this patent is extended or adjusted under 35 U.S.C. 154(b) by 811 days.

(21) Appl. No.: 17/793,813

(22) PCT Filed: Aug. 5, 2020

(86) PCT No.: PCT/CN2020/107165
§ 371 (c)(1),
(2) Date: Jul. 19, 2022

(87) PCT Pub. No.: WO2021/223338
PCT Pub. Date: Nov. 11, 2021

(65) Prior Publication Data
US 2023/0083219 A1 Mar. 16, 2023

(30) Foreign Application Priority Data

May 8, 2020 (CN) .......................... 202010383821.3

(51) Int. Cl.
*A61K 39/04* (2006.01)
*A61K 39/00* (2006.01)
(Continued)

(52) U.S. Cl.
CPC .............. *A61K 39/04* (2013.01); *A61P 13/10* (2018.01); *A61P 35/00* (2018.01);
(Continued)

(58) Field of Classification Search
CPC .............. C07K 14/245; C07K 2319/02; A61K 39/04; A61K 2039/523; A61K 2039/585;
(Continued)

(56) References Cited

FOREIGN PATENT DOCUMENTS

| CN | 102327604 A | * | 1/2012 |
| CN | 105008539 A | | 10/2015 |

(Continued)

OTHER PUBLICATIONS

Sokurenko et al. (1998). "Pathogenic adaptation of *Escherichia coli* by natural variation of the FimH adhesin". Proc. Natl. Acad. Sci. USA, 95(15):8922-8926. (Year: 1998).*

(Continued)

*Primary Examiner* — Daniel E Kolker
*Assistant Examiner* — Bailey M Morgan
(74) *Attorney, Agent, or Firm* — JC ONE WORLD

(57) ABSTRACT

Recombinant BCG, a preparation method therefor and an application thereof. A shuttle plasmid that can express a FimH protein on the surface of BCG is constructed, and a gene fragment that expresses the FimH protein is transformed into wild-type BCG to thereby obtain recombinant BCG. Upon verification, the recombinant BCG can express the FimH protein on the surface of BCG; therefore, the BCG can specifically bind to subjects that can selectively bind to the FimH protein. The recombinant BCG can also enhance the local innate immune effect and adaptive immune effect induced by BCG and the anti-tumor effect of peripheral blood mononuclear cells, and also significantly improves the effect of BCG against bladder tumors, and is used to treat bladder tumors.

4 Claims, 13 Drawing Sheets

Specification includes a Sequence Listing.

Branch chain of mannose

Branch chain of mannose

FimH protein

(51) Int. Cl.
_A61P 13/10_ (2006.01)
_A61P 35/00_ (2006.01)

(52) U.S. Cl.
CPC .................. _A61K 2039/523_ (2013.01); _A61K 2039/585_ (2013.01); _C07K 2319/02_ (2013.01)

(58) Field of Classification Search
CPC .......... A61P 13/10; A61P 35/00; C12N 15/74; C12N 1/205; C12R 2001/32
See application file for complete search history.

(56) References Cited

FOREIGN PATENT DOCUMENTS

| | | |
|---|---|---|
| CN | 106029090 A | 10/2016 |
| WO | 2018184188 A1 | 10/2018 |

OTHER PUBLICATIONS

ThermoFisher. (2018). "Restriction Enzyme Basics" as obtained online at web.archive.org/web/20181017214358/http://www. thermofisher.com/us/en/home/life-science/cloning/cloning-learning-center/invitrogen-school-of-molecular-biology/molecular-cloning/restriction-enzymes/restriction-enzyme-basics (Year: 2018).*

Newman et al. (1995). "Structure of BamHI Endonuclease Bound to DNA: Partial Folding and Unfolding on DNA Binding." Science, 269(5224):656-663. (Year: 1995).*

Machine translation of CN 102327604 A as obtained online at worldwide.espacenet.com [Accessed on Jun. 12, 2025]. (Year: 2012).*

Ingersoll and Albert. (2013). "From infection to immunotherapy: host immune responses to bacteria at the bladder mucosa". Mucosal Immunol., 6(6):1041-1053. (Year: 2013).*

International Search Report for PCT Patent Application No. PCT/CN2020/107165 dated Feb. 8, 2021, 10 pages (6 pages of Official copy and 4 pages of English translation).

Karam et al., "Vaccination with Recombinant FimH Fused with Flagellin Enhances Cellular and Humoral Immunity Against Urinary Tract Infection in Mice", Vaccine, vol. 31, 2013, pp. 1210-1216.

Spaulding et al., "Selective Depletion of Uropathogenic _E. coli_ from the Gut by a FimH Antagonist", Nature, vol. 546, Jun. 22, 2017, pp. 528-545.

* cited by examiner

Fig. 6C                              Fig. 6D

SEQUENCE LISTING

<160> NUMBER OF SEQ ID NOS: 3

<210> SEQ ID NO 1
<211> LENGTH: 62
<212> TYPE: DNA
<213> ORGANISM: Artificial Sequence
<220> FEATURE:
<223> OTHER INFORMATION: 19ss Signal peptide

<400> SEQUENCE: 1
tatgaagcgt ggactgacgg tcgcggtagc cggagccgcc attctggtcg caggtctttc      60
cg      62

<210> SEQ ID NO 2
<211> LENGTH: 53
<212> TYPE: DNA
<213> ORGANISM: Artificial Sequence
<220> FEATURE:
<223> OTHER INFORMATION: Primer F -continued

```
<400> SEQUENCE: 2
ctggtgccgc gcggcagcca tatgatgaaa cgagttatta ccctgtttgc tgt          53

<210> SEQ ID NO 3
<211> LENGTH: 55
<212> TYPE: DNA
<213> ORGANISM: Artificial Sequence
<220> FEATURE:
<223> OTHER INFORMATION: Primer R

<400> SEQUENCE: 3
agtggtggtg gtggtggtgc tcgagaaact ggaaatcatc gctgttatag ttgtt          55
```

RECOMBINANT BCG, PREPARATION METHOD THEREFOR AND APPLICATION THEREOF

CROSS-REFERENCE TO RELATED APPLICATIONS

This application is a U.S. national phase entry of, and claims priority to PCT International Phase Application No. PCT/CN2020/107165, filed Aug. 5, 2020, which claims priority to Chinese Patent Application No. CN202010383821.3, filed May 8, 2020. The entire contents of the above-referenced applications and of all priority documents referenced in the Application Data Sheet filed herewith are hereby incorporated by reference for all purposes.

INCORPORATION-BY-REFERENCE OF SEQUENCE LISTING

The present application is being filed along with a Sequence Listing in electronic format. The Sequence Listing is provided as a file entitled EANA-2022009pSEQLIST.txt, which is 973 bytes in size, created and last modified on Jul. 11, 2022. The information in the accompanying Sequence Listing is incorporated by reference in its entirety into this application.

FIELD

The invention belongs to the technical field of medicine, and relates to a recombinant Bacille Calmette-Guérin (BCG), in particular to a recombinant BCG capable of expressing a FimH protein after recombination, and a preparation method therefor and application thereof.

BACKGROUND

Urothelial carcinoma of bladder is one of the common malignant tumors in the urinary system. Bladder cancer is divided into non-muscle-invasive bladder cancer (superficial) and muscle-invasive bladder cancer, of which superficial bladder cancer accounts for about 75%-80%. At present, the standard clinical treatment for bladder cancer is an intravesical instillation after transurethral resection. Because of the high recurrence rate with surgical resection, the intravesical instillation in later stage is the key to prolonging patient's life. The most effective immunotherapy in clinical practice is BCG instillation, which kills tumors by activating immune cells. As being the preferred intravesical instillation medicament for intermediate- and high-risk superficial bladder cancers, BCG's anti-tumor effect depends on the adhesion to epithelial cells of bladder, and the BCG is further phagocytosed by macrophages and induces a series of immune responses to kill tumor cells. Increasing the dose of BCG can enhance its anti-bladder tumor effect, but it can also cause local inflammatory reactions, resulting in significant local irritation symptoms such as frequent urination, urgent micturition, and dysuria. The severity of adverse reactions is positively correlated with the dose of BCG. At present, the biggest problem of using BCG instillation for the treatment of bladder cancer is that the ability of BCG to adhere to tumor cells and epithelial cells of bladder is insufficient and the selectivity thereof is low, which may lead to a low immune response, being unfavourable for anti-tumor effect. Simply increasing the dose may significantly aggravate adverse reactions, including adhesions such as frequent urination, urgent micturition, dysuria, fever and even systemic infection.

An article in Nature in 2017 (Selective depletion of uropathogenic *E. coli* from the gut by a FimH antagonist, Caitlin N. Spaulding, Roger D. Klein, Ségolène Ruer, Andrew L. Kau, Henry L. Schreiber, Zachary T Cusumano, Karen W. Dodson, Jerome S. Pinkner, Daved H. Fremont, James W. Janetka, Han Remaut, Jeffrey I. Gordon & Scott J. Hultgren, Nature volume 546, pages 528-532 (2017)), describes the FimH protein of *Escherichia coli* can specifically recognize mannose. The FimH protein can improve the antigen presentation ability of a dendritic cell through the TLR4 pathway. The surface of a bladder cancer cell is rich in mannose residues, and bladder tumor cells are not only the target cells of killer lymphocytes induced by BCG, but also can participate in immune activities as antigen-presenting cells. Therefore, engineering a wild-type BCG so that the FimH protein can be expressed on the surface of BCG can improve the ability of BCG to adhere to epithelial cells and tumor cells, thereby improving the anti-tumor effect of BCG, enhancing the targeting of BCG to bladder tumors, and improving the anti-tumor effect of BCG, while reducing the dose of BCG and reducing the adverse reactions it induced.

SUMMARY

The purpose of the present invention is to provide a recombinant BCG, preparation method therefor and application thereof. The recombinant BCG recombined with FimH protein is obtained by engineering a wild type BCG. The recombinant BCG can better adhere to bladder epithelium and bladder cancer cells, so that the effect of BCG instillation therapy can be improved, or the dose of BCG instillation can be reduced while having the same or similar effect. In order to obtain the above-mentioned recombinant BCG, a shuttle plasmid capable of expressing a FimH protein on the surface of BCG is constructed herein using genetic engineering technologies, and the plasmid is transformed into a wild-type BCG by electroporation. The wild-type BCG comes from: ATCC®35734, which is a resource freely available to the public. The present application addresses the deficiencies in the prior art.

The purpose of the present invention described above can be achieved with the following technical solutions:

In one aspect, the present invention provides a novel recombinant BCG, which can express a FimH protein on its own surface. The recombinant BCG has been deposited. Depositary authority: China General Microbiological Culture Collection Center; address: No. 3, Yard 1, Beichen West Road, Chaoyang District, Beijing, Institute of Microbiology, Chinese Academy of Sciences; accession number: 19540; deposition date: Apr. 17, 2020; it is classified as *Mycobacterium bovis*, named *Mycobacterium bovis* in Latin.

Further, the recombinant BCG, via the FimH protein expressed on its surface, specifically binds to subjects with FimH protein-binding properties (the subjects are substances capable of binding to the FimH protein).

Further, the subjects with FimH protein-binding properties include tumor cells, preferably, the tumor cells include, but are not limited to, bladder cancer tumor cells.

Further, the recombinant BCG is a novel BCG obtained by transforming a plasmid containing a FimH protein-expressing gene on its surface into a wild-type BCG.

Further, the FimH protein-expressing gene is inserted within the plasmid by a 19ss signal peptide-expressing gene; preferably, the sequence of the 19ss signal peptide is:

(SEQ ID No.: 1)
TATGAAGCGTGGACTGACGGTCGCGGTAGCCGGAGCCGCCATTCTG

GTCGCAGGTCTTTCCG.

In another aspect, the present invention provides a method for the preparation of a recombinant BCG, the method comprises the following steps: S1: using a plasmid as a vector, fusing a FimH protein-expressing gene with a 19ss signal peptide-expressing gene, and inserting them together into the vector after fusion, then the 19ss signal peptide-expressing gene will carry the FimH protein-expressing gene to the surface of a bacteria to form a new plasmid; S2: transforming the new plasmid obtained in S1 into a wild-type BCG.

Further, in S1, the plasmid is pMV261; the FimH protein-expressing gene described in S1 is from *Escherichia coli*; and in S1, the addition of an enzyme and a primer for enzyme cleavage is required, the cleavage sites of this enzyme are BamHI and Hind III, so that the FimH protein-expressing gene and the 19ss signal peptide-expressing gene are inserted between BamHI and Hind III; the primer for enzyme cleavage is:

(SEQ ID No.: 2)
F: 5'CTGGTGCCGCGCGGCAGCCATATGATGAAACGAGTTATTAC

CCTGTTTGCTGT (SEQ ID No.: 3)
R: 5'AGTGGTGGTGGTGGTGGTGCTCGAGAAACTGGAAATCATCG

CTGTTATAG TTGTT

In another aspect, the present invention provides a bladder tumor inhibitor, the inhibitor is the recombinant BCG described in any of the above paragraphs, and the recombinant BCG is a BCG which is capable of specifically binding to bladder cells to inhibit bladder tumors and is capable of enhancing the anti-bladder tumor effect of peripheral blood mononuclear cells, thus achieving the treatment for tumor. For example, the BCG can bind to bladder cancer by specifically binding to the mannose residues on bladder cancer, thereby achieving the inhibition or treatment for bladder cancer cells.

In another aspect, the present invention provides an immune effect promoter, the immune effect promoter comprises a promoter capable of enhancing the local innate immune effect and adaptive immune effect induced by BCG, and the promoter comprises the recombinant BCG described in any of the above paragraphs.

In another aspect, the present invention provides the use of a novel BCG in the preparation of a therapeutic medicament, the novel BCG is the recombinant BCG capable of expressing a FimH protein on its own surface described in any of the above paragraphs, and the medicament includes an anti-tumor medicament and a medicament for enhancing immune effects.

Further, the anti-tumor medicament includes an anti-bladder cancer medicament, and the medicament for enhancing immune effects includes a medicament for enhancing the local innate immune effects induced by BCG and a medicament for enhancing adaptive immune effects.

The above innovation work has the following effects:
1. The FimH protein is fused creatively into the BCG which can express the protein on its surface, thereby obtaining a novel recombinant BCG strain, which can express the FimH protein on its surface commendably, and can specifically bind to subjects with FimH protein-binding properties, for example, specifically bind to mannose residues on bladder cancer cells.
2. The recombinant BCG obtained herein has strong adhesion and internalization to bladder epithelial cells. The adhesion and internalization to bladder tumor cells are enhanced, and the retention time becomes longer, which is beneficial to inhibit or eliminate tumors.
3. Compared with common BCG, the recombinant BCG has stronger adhesion to bladder cancer cells. The amount of adhesion in this phenomenon would be decreased after the addition of D-mannose for competitive inhibition, indicating that the recombinant BCG rBCG-S.FimH improves its adhesion to bladder cancer cells through the binding of the FimH protein to mannose residues on the surface of bladder cancer cells.
4. Recombinant BCG can enhance the anti-tumor effect of peripheral blood mononuclear cells.
5. Recombinant BCG can significantly enhance the local innate immune effect and adaptive immune effect (Th1 effect) induced by BCG, and the recombinant BCG has significantly better enhancement effect as compared to FimH protein and traditional BCG, and the mechanism thereof is also different from that of FimH. More importantly, the recombinant BCG can enhance the immune effect and enhance the killing effect for tumor cells.
6. The recombinant BCG rBCG-S.FimH can effectively reduce the weight of bladder cancer cells, and it has been known from a number of experiments that nearly 40% of the tumors can disappear completely after the treatment with the recombinant BCG herein. Therefore, the recombinant BCG rBCG-S.FimH has stronger anti-tumor effect and has better treatment effect for bladder cancers than current conventional treatments.
7. It should also be noted that the recombinant BCG herein not only has an elimination effect on bladder cancer cells, but also has a better curative effect for other cancers.

In conclusion, the recombinant BCG constructed in the present application has stronger ability to adhere and internalize into cancer cells in vivo and in vitro than the BCG that has not been modified in a similar manner of the present invention, and enhance the immune effect to kill tumor cells. The recombinant BCG of the present invention can achieve the effect of anti-tumor (such as anti-bladder cancer), simultaneously by specifically binding to tumors (such as bladder cancer), by enhancing immunity, and by enhancing the anti-tumor effect of peripheral blood mononuclear cells, etc. The synergistic effect of multiple manners greatly increases the anti-tumor effect of the recombinant BCG, realizing the treatment for tumor. Therefore, the recombinant BCG has an excellent potential clinical application prospect.

BRIEF DESCRIPTION OF DRAWINGS

In order to illustrate the technical solutions in the examples of the present invention more clearly, the accompanying drawings used in the description of the examples will be described briefly in the following. Obviously, the accompanying drawings in the following description are only some examples of the present invention. For those of ordinary skill in the art, other drawings can also be obtained from these drawings without creative effort.

FIGS. 6C and 6D are both histograms showing the binding of recombinant BCG rBCG-s.EGFP and rBCG-S.FimH-EGFP after incubation with bladder cancer cells for 4 hours.

DETAILED DESCRIPTION

Figure 1:
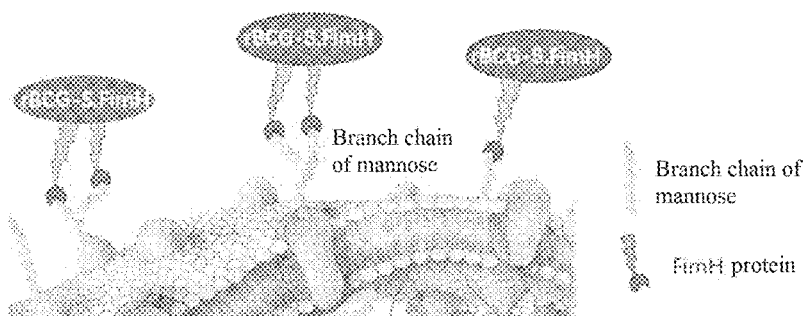
FIG. 1 is a schematic diagram of the surface structure of a bladder cancer cell.

The examples of the present invention are described below in detail, the legend of which is illustrated in the accompanying drawings, wherein the same or similar reference numerals throughout refer to the same or similar elements or elements having the same or similar functions. The examples described below with reference to the accompanying drawings are exemplary, only used to explain the present invention, and should not be construed as a limitation of the present invention.

Example 1

A recombinant BCG, which is capable of expressing a FimH protein on its surface, so as to specifically bind to subjects with FimH protein-binding properties using the FimH protein expressed on its surface. Therefore, the recombinant BCG theoretically should be capable of playing an active and significant role in any occasion where the BCG is required to specifically bind to a target via the FimH protein.

Figure 2:
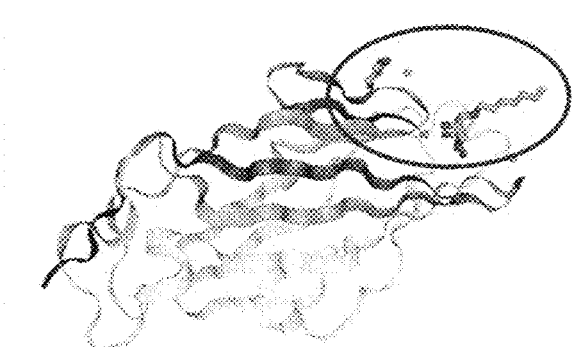
FIG. 2 is a schematic diagram of the co-crystallization for the binding of FimH protein and D-mannose.

The recombinant BCG can express a FimH protein on its surface, so that it can better specifically bind to bladder cancers. As shown in FIG. 1, the surface of a bladder cancer cell is rich in mannose residues, and the FimH protein expressed on the surface of the recombinant BCG can bind to mannose residues, thereby enhancing the specificity of the recombinant BCG to bind to bladder cancer cells and improving the immune efficacy. FIG. 2 shows the co-crystal structure of the protein with FimH and mannose residues, and the part in the circle is the domain of FimH that recognizes mannose residues.

The specific embodiment for preparing the recombinant BCG is as follows:

S1: selecting the pMV261 plasmid with kanamycin resistance (i.e., the pMV261 vector), and adding an enzyme, a primer for enzyme cleavage, a 19ss anchor protein (i.e., 19ss signal peptide)-expressing gene and a FimH protein-expressing gene to construct pMV261-S.FimH plasmid, i.e., the new plasmid;

In this step, the 19ss anchor protein-expressing gene was firstly fused with the FimH protein-expressing gene, and then the 19ss anchor protein-expressing gene was inserted behind the promoter HSP60, so that the FimH protein-expressing gene was carried to the surface of a bacteria, enabling the BCG to express the FimH protein on its surface;

S2: transforming the new plasmid obtained in S1 into a wild-type BCG by electroporation, that is, constructing the recombinant BCG rBCG-S.FimH.

Figure 3:
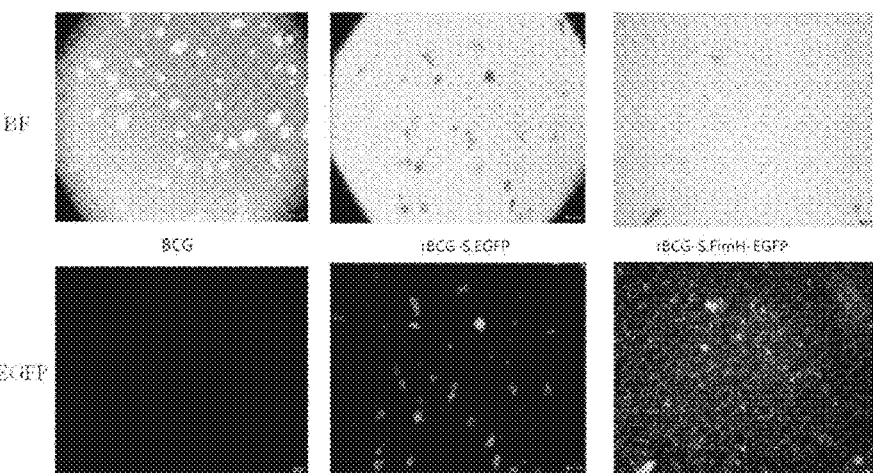
FIG. 3 shows the verification of the expressions of BCG and recombinant BCG.

For the convenience of fluorescence detection, the wild-type BCG with EGFP tag and the recombinant BCG with EGFP tag and fused with the FimH protein expressed on the surface were constructed in the same way, which were described as rBCG-S.EGFP and rBCG-S.FimH-EGFP, respectively. The purpose for EGFP addition was that green fluorescence could be observed under a fluorescence microscope without changing other functions of the BCG. Therefore, rBCG-S.EGFP and rBCG-S.FimH-EGFP could emit green light under a fluorescence microscope, which is convenient for fluorescence detection, as shown in FIG. 3.

In the above preparation process, the key information involved is as follows:

The cleavage sites of the enzyme in S1 are BamHI and Hind III, and the 19ss anchor protein-expressing gene was synthesized together with the FimH protein-expressing gene, and then inserted as a whole between the two cleavage sites. The 19ss anchored protein-expressing gene was derived from BCG.

The primer for enzyme cleavage is:

```
(SEQ ID No.: 2)
F: 5'CTGGTGCCGCGCGGCAGCCATATGATGAAACGAGTTATTAC

CCTGTTTGCTGT (SEQ ID No.: 3)
R: 5'AGTGGTGGTGGTGGTGGTGCTCGAGAAACTGGAAATCATCG

CTGTTATAG TTGTT
```

The 19ss signal peptide sequence is:

```
                                    (SEQ ID No.: 1)
TATGAAGCGTGGACTGACGGTCGCGGTAGCCGGAGCCGCCATTCTG

GTCGCAGGTCTTTCCG.
```

The inventors creatively fused FimH into BCG, thereby obtaining a novel BCG strain which is capable of expressing the recombinant FimH protein of a FimH protein on the surface. The recombinant BCG strain has been deposited at China General Microbiological Culture Collection Center in 2020 (Address: No. 3, Yard 1, Beichen West Road, Chaoyang District, Beijing), accession number: 19540, which is classified as *Mycobacterium bovis*, named *Mycobacterium bovis* in Latin.

Figure 4:
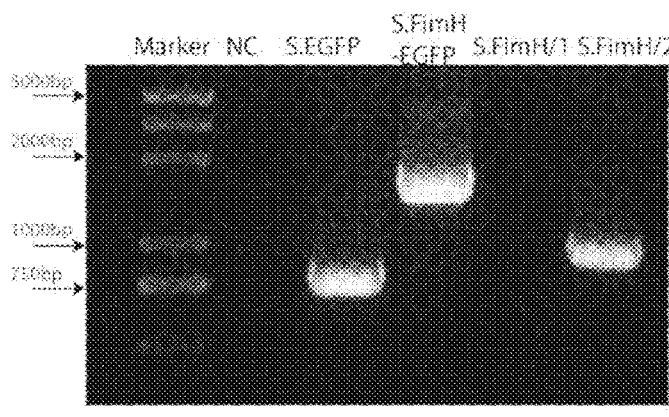
FIG. 4 shows the RT-PCR gel electrophoresis of the recombinant BCG.
Figure 5A:
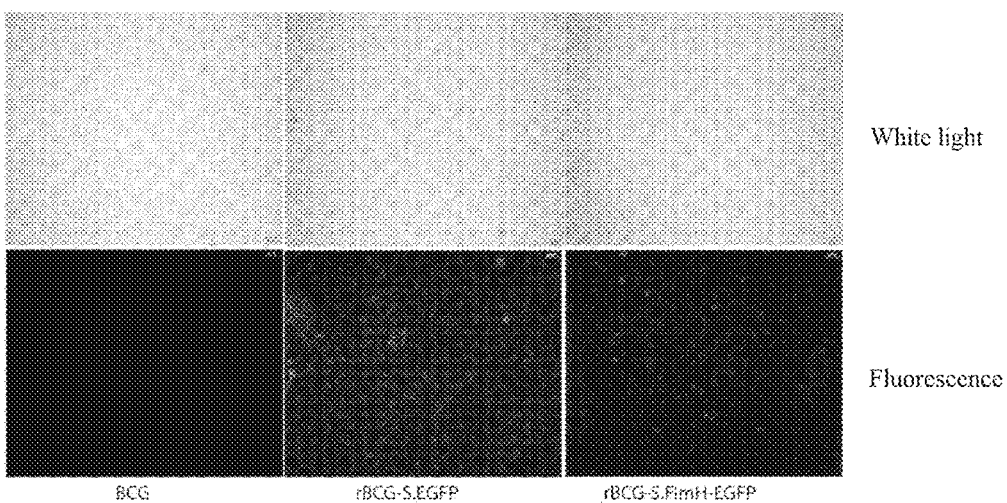
FIG. 5A is an image of rBCG-S.EGFP and rBCG-S.FimH-EGFP under fluorescence.
Figures 5B, 5C:
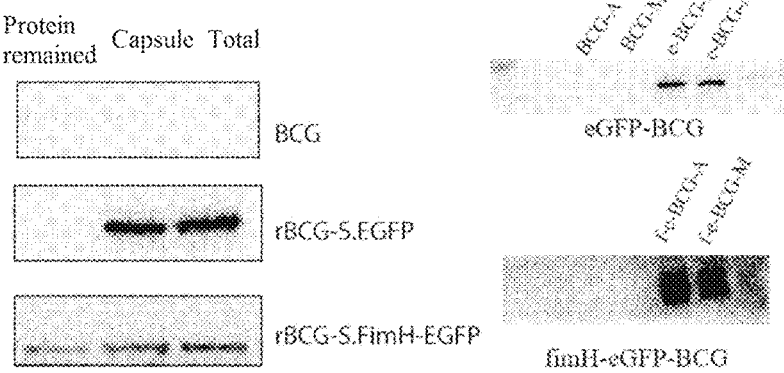
FIG. 5B shows the verification that whether a capsule protein is expressed on a membrane by extracting the capsule protein of BCG.
FIG. 5C shows the western blot of rBCG-S.EGFP and BCG-S.FimH-EGFP detected by EGFP antibody.

It was confirmed by RT-PCR gel electrophoresis that the above-mentioned recombinant BCG can be successfully transcribed into mRNA, as shown in FIG. 4. FIG. 4 shows the RT-PCR gel electrophoresis of the recombinant BCG, from which it can be seen that the recombinant BCG can be successfully transcribed into mRNA. It was verified by western blot with TritonX-114 membrane extraction reagent that most of the proteins could be expressed on the membrane surface of BCG, as shown in FIG. 5B.

Further researches showed that the recombinant BCG constructed in the present application has stronger ability to adhere and internalize into cancer cells in vivo and in vitro than the BCG that has not been modified in a similar manner of the present invention, so the recombinant BCG of the present invention can recruit more monocytes/macrophages to infiltrate cancer cells, which further strengthening the local immune efficacy and improving the anti-tumor effect thereof.

Example 2

Constructing rBCG-S.FimH that expresses the FimH protein on the capsule surface, which comprises the followings: selecting the pMV261 plasmid with kanamycin resistance, inserting the 19ss anchor protein-expressing gene behind the promoter HSP60, constructing plasmids such as pMV261-S.EGFP, pMV261-S.FimH-EGFP and pMV261-S.FimH respectively. Electrotransfection was used to construct rBCG-S.EGFP, rBCG-S.FimH-EGFP and rBCG-S.FimH. Best monoclonal strains were screened for kanamycin resistance. Fluorescence of the recombinant plasmid was observed under a green light by fluorescence microscope. Transcription of the recombinant plasmid was verified at a cDNA level by RT-PCR experiments; and the protein expression of the recombinant BCG was verified at a protein level by western blot experiments. Referring to FIGS. 2, 4 and 5. FIG. 5A shows that both rBCG-S.EGFP and rBCG-S.FimH-EGFP can emit green fluorescence under 488 nm fluorescence excitation. FIG. 5B shows that most of the recombinant proteins can be expressed on the membrane by extracting the capsule protein of BCG, which indirectly proved that the S.FimH protein was expressed on the capsule of BCG. FIG. 5C shows that the proteins transferred into BCG by the plasmid can be expressed normally in BCG. FIG. 2 shows the co-crystal structure of the protein with FimH and D-mannose, and the part in the circle is the domain of FimH that recognizes mannose residues. FIG. 4 shows in RT-PCR experiment, all of rBCG-S.EGFP, rBCG-S.FimH-EGFP and rBCG-S.FimH can transcribe the protein inserted by the plasmid.

In this example, rBCG-S.FimH expressing the FimH protein on the capsule surface was successfully constructed.

Figure 6A:
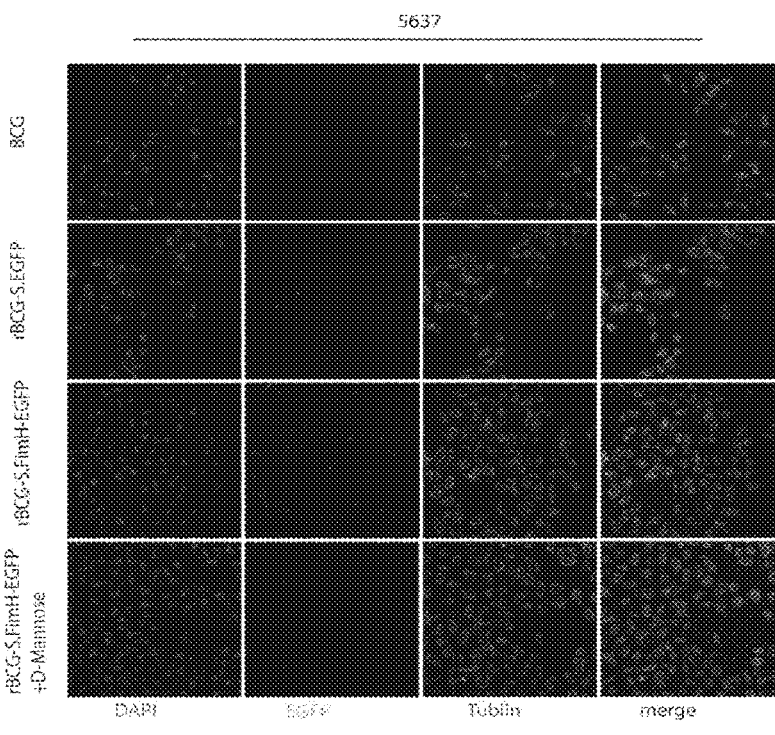
FIGS. 6A and 6B are both the fluorescence results showing the binding of recombinant BCG rBCG-s.EGFP and rBCG-S.FimH-EGFP after incubation with bladder cancer cells for 4 hours.

Example 3 rBCG-S.EGFP and rBCG-S.FimH-EGFP were respectively incubated with human bladder cancer cell line 5637 for 4 hours, or D-mannose was added in the case of rBCG-S.FimH-EGFP for competitive inhibition. Four hours after which, the medium was discarded. Then the nuclei were fixed and stained with DAPI, and photographed by a confocal microscope. The recombinant BCG rBCG-S.EGFP and rBCG-S.FimH-EGFP were obtained according to the method in the present invention, and the human bladder cancer cell line 5637 was obtained from Shanghai Institutes for Biological Sciences, Chinese Academy of Sciences. As shown in FIGS. 6A and 6C, FIGS. 6A and 6C are the fluorescence results showing the binding of rBCG-S.EGFP and rBCG-S.FimH-EGFP after respectively incubation with human bladder cancer cell line 5637 for 4 hours, or after addition of D-mannose for competitive inhibition. It can be seen from FIGS. 6A and 6C that the recombinant BCG rBCG-S.FimH-EGFP has stronger fluorescent quantum dot and adhesion, and when D-mannose was added for competitive inhibition, the amount of adhesion of the recombinant BCG rBCG-S.FimH-EGFP could be decreased, which indicates that the recombinant BCG rBCG-S.FimH-EGFP can bind with mannose residues on the surface of bladder cancer cells.

At the same time, referring to Table 1, the experimental data showed that the recombinant BCG rBCG-S.FimH- EGFP has stronger adhesion to bladder cancer cells. The addition of D-mannose for competitive inhibition decreased the amount of adhesion.

TABLE 1

Fluorescence values of 5637 cells under different incubation conditions (i.e., the amount of BCG adhered and internalized into cells)

| | rBCG-S.EGFP, incubated for 4 hours | rBCG-S.Fimh-EGFP, incubated for 4 hours | rBCG-S.Fimh-EGFP and 100 uM D- mannose added, incubated for 4 hours |
|---|---|---|---|
| 1 | 190 | 783 | 130 |
| 2 | 202 | 865 | 98 |
| 3 | 211 | 729 | 78 |

The above results indicated that through the binding of the transformed FimH protein to the mannose residues on the surface of bladder cancer cells, the recombinant BCG rBCG-S.Fimh-EGFP significantly improves the adhesion of BCG to bladder cancer cells.

Figure 6B:
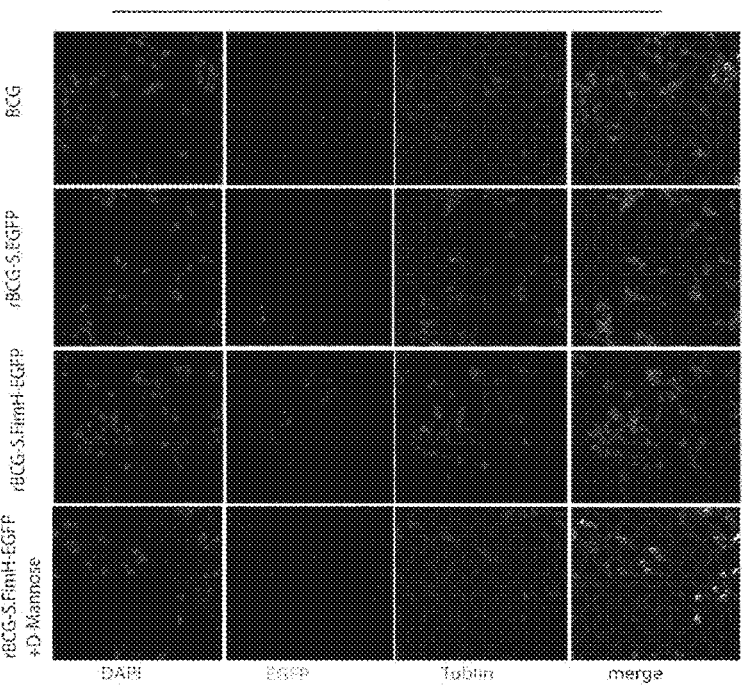

Example 4 rBCG-S.EGFP and rBCG-S.Fimh-EGFP were respectively incubated with mouse bladder cancer cell line MB49 for 4 hours, or D-mannose was added for competitive inhibition. Four hours after which, the medium was discarded. Then the nuclei were fixed and stained with DAPI, and photographed by a confocal microscope. rBCG-S.EGFP and rBCG-S.Fimh-EGFP were obtained according to the method in the invention, and the mouse bladder cancer cell line MB49 was obtained from ATCC. As shown in FIGS. 6B and 6D, FIGS. 6B and 6D are the fluorescence results showing the binding of rBCG-S.EGFP and rBCG-S.Fimh-EGFP after incubation with bladder cancer cells for 4 hours. rBCG-S.EGFP and rBCG-S.Fimh-EGFP were respectively incubated with mouse bladder cancer cell line MB49 for 4 hours, or D-mannose was added for competitive inhibition. It can be seen from FIGS. 6B and 6D that the recombinant BCG rBCG-S.Fimh-EGFP has stronger fluorescent quantum dot and adhesion, and when D-mannose was added for competitive inhibition, the amount of adhesion of the recombinant BCG rBCG-S.Fimh-EGFP could be decreased, which indicates that the recombinant BCG rBCG-S.Fimh-EGFP can bind with mannose residues on the surface of bladder cancer cells.

At the same time, referring to Table 2, the experimental data showed that the recombinant BCG rBCG-S.Fimh-EGFP has stronger adhesion to bladder cancer cells and the addition of D-mannose for competitive inhibition decreased the amount of adhesion, indicating that through the binding of the transformed FimH protein to the mannose residues on the surface of bladder cancer cells, the recombinant BCG rBCG-S.Fimh-EGFP improves the adhesion of BCG to bladder cancer cells.

TABLE 2

Fluorescence values of MB49 cells under different incubation conditions (i.e., the amount of BCG adhered and internalized into cells)

| | rBCG-S.EGFP, incubated for 4 hours | rBCG-S.Fimh-EGFP, incubated for 4 hours | rBCG-S.Fimh-EGFP and 100 uM D- mannose added, incubated for 4 hours |
|---|---|---|---|
| 1 | 284 | 1253 | 200 |
| 2 | 306 | 1338 | 165 |
| 3 | 299 | 1296 | 138 |

Figure 7A:
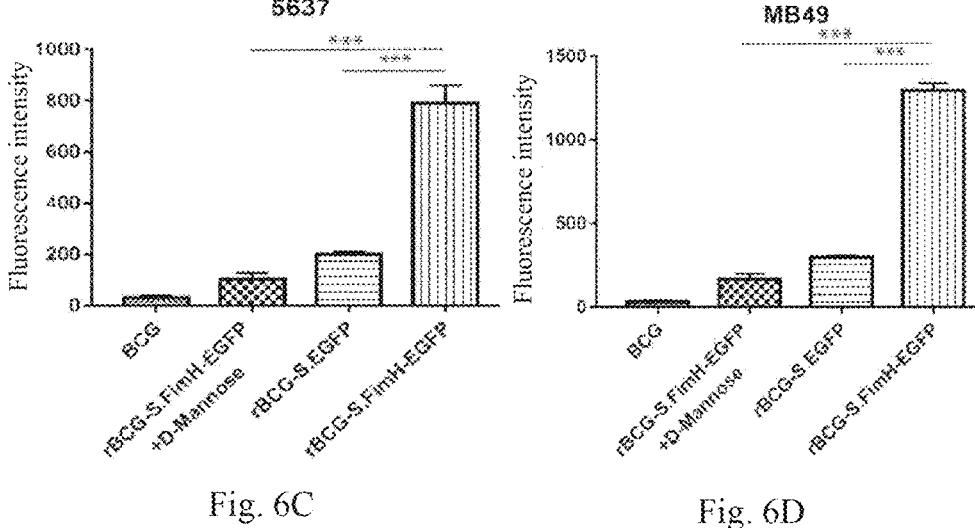
FIG. 7A is the fluorescence result showing the binding of rBCG-S.EGFP and rBCG-S.FimH-EGFP after incubation respectively with different bladder cancer cells for 10 hours.
Figure 7A:
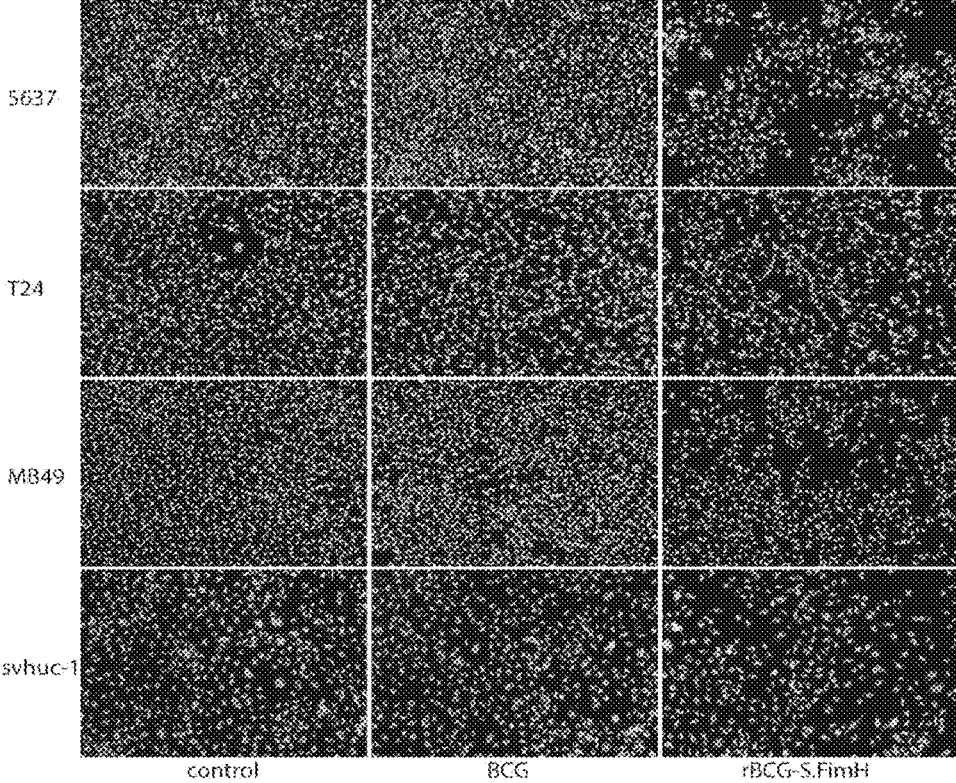
Figure 7B:
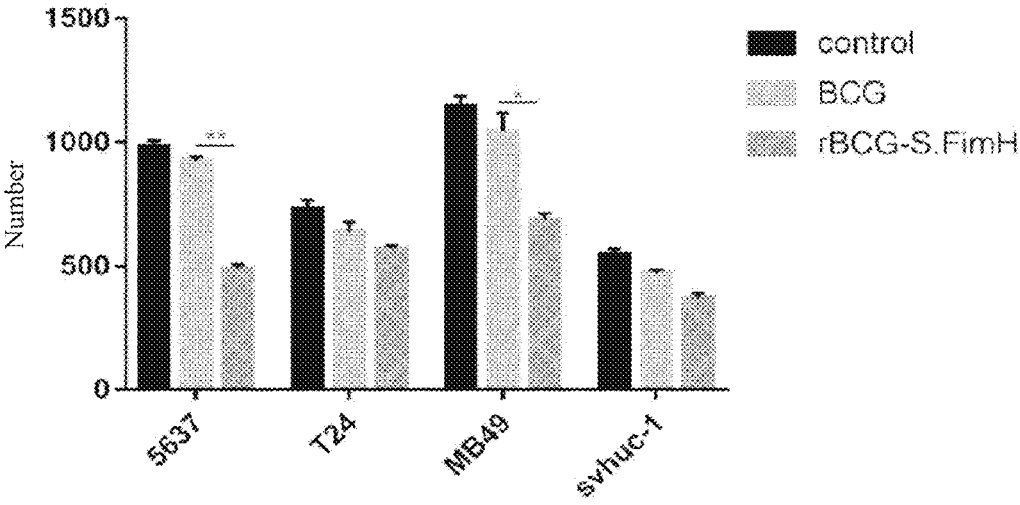
FIG. 7B is a histogram showing the binding of rBCG-s.EGFP and rBCG-S.FimH-EGFP after incubation respectively with different bladder cancer cells and normal urothelial cells for 10 hours.

Example 5 rBCG-S.EGFP and rBCG-S.Fimh-EGFP were co-incubated respectively with human bladder cancer cell line 5637, mouse bladder cancer cell line MB49, T24 and svhuc-1 for 10 hours. After which, the nuclei were stained with DAPI and areas were captured randomly with high-throughput fluorescence. rBCG-S.EGFP and rBCG-S.Fimh-EGFP were obtained according to the method in the present invention, and the human bladder cancer cell line 5637 was obtained from Shanghai Institutes for Biological Sciences, Chinese Academy of Sciences, and the mouse bladder cancer cell lines MB49 and MBT-2 were obtained from ATCC. As shown in FIGS. 7A and 7B, FIGS. 7A and 7B are the fluorescence results showing the binding of rBCG-S.EGFP and rBCG-S.Fimh-EGFP after incubation respectively with different bladder cancer cell lines for 10 hours.

The experimental results showed that the recombinant BCG rBCG-S.Fimh-EGFP has a significantly enhanced growth inhibition effect on bladder cancer cells as compared with the recombinant BCG rBCG-S.EGFP.

Example 6

An orthotopic model of mouse bladder cancer was established, and the experimental subjects were C57 mice with mouse bladder cancer cell line MB49-luc implanted in situ, with 8 mice in each group. The experiment included control group, FimH group, BCG group and recombinant BCG group. The control group was instilled with 50 µl of PBS, the FimH group was instilled with 5 ug of FimH protein in 50 ul of PBS, the BCG group was instilled with 50 µl of BCG with an OD value of 0.15, and the recombinant BCG group was instilled with 50 µl of recombinant BCG rBCG-S.FimH with an OD value of 0.15. The instillation was performed twice a week for 3 weeks. Experimental subjects were tested after three weeks.

Figure 8A:
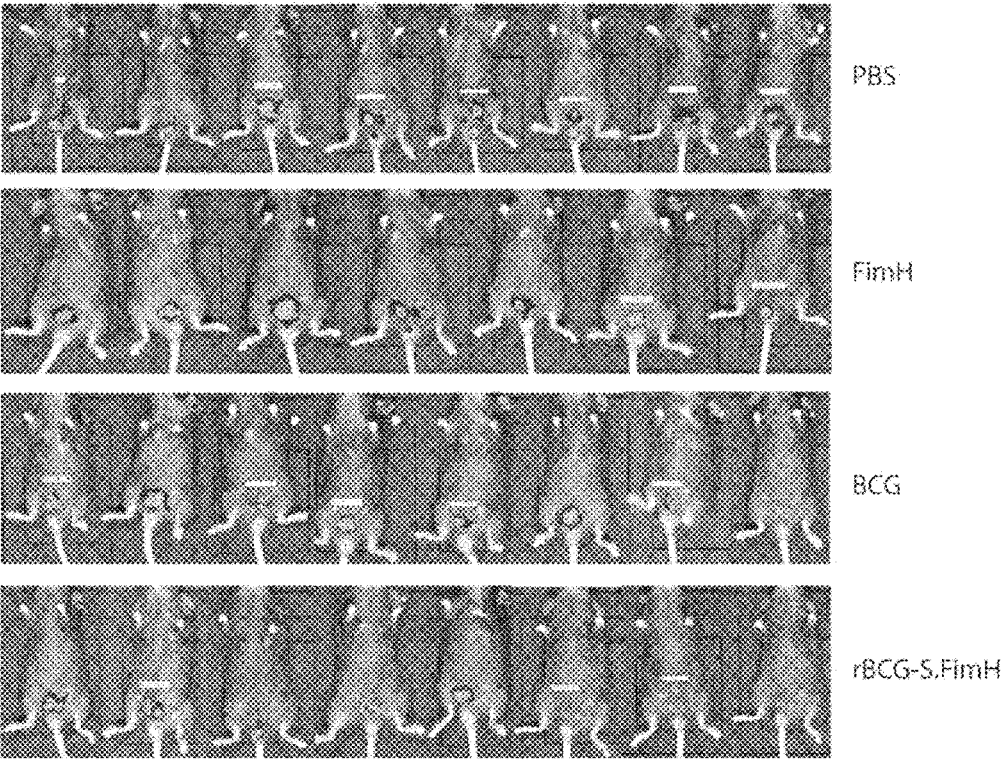
FIG. 8A shows the comparison of living imaging for C57/BL6 mouse with tumor cells (MB49) implanted in bladder after treating with different BCG instillations for three weeks.
Figure 8B:
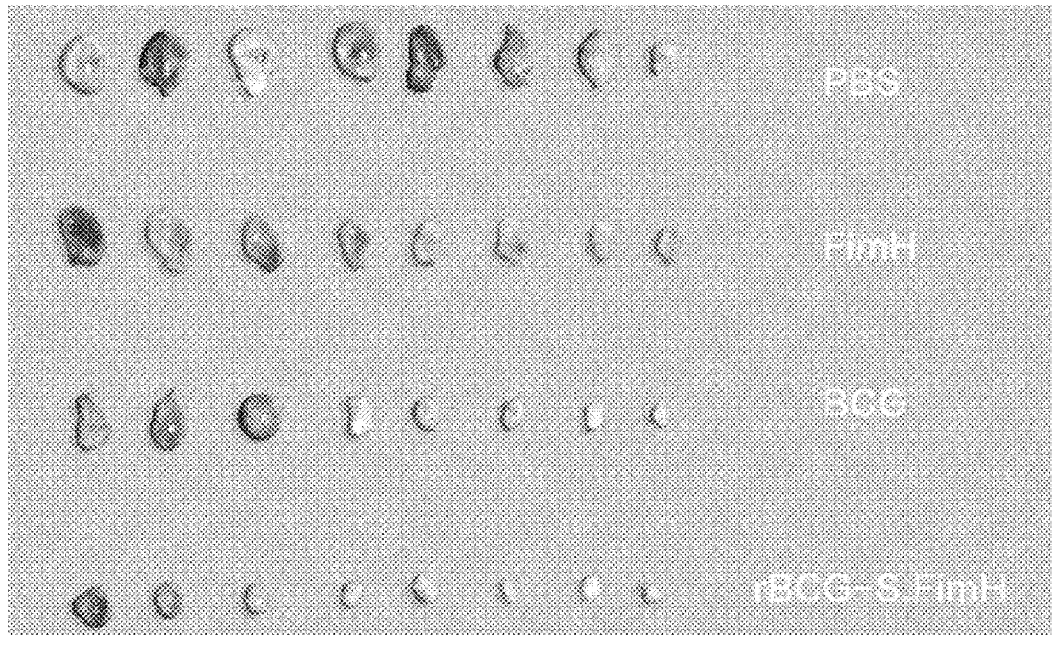
FIG. 8B shows the comparison of the sizes of mouse bladder samples.
Figure 8C:
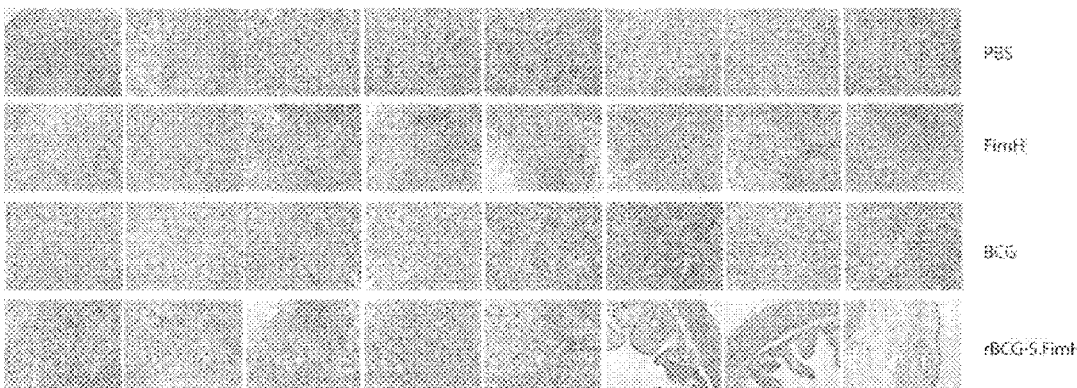
FIG. 8C shows the comparison for tissue slices of mouse bladders.
Figure 8D:
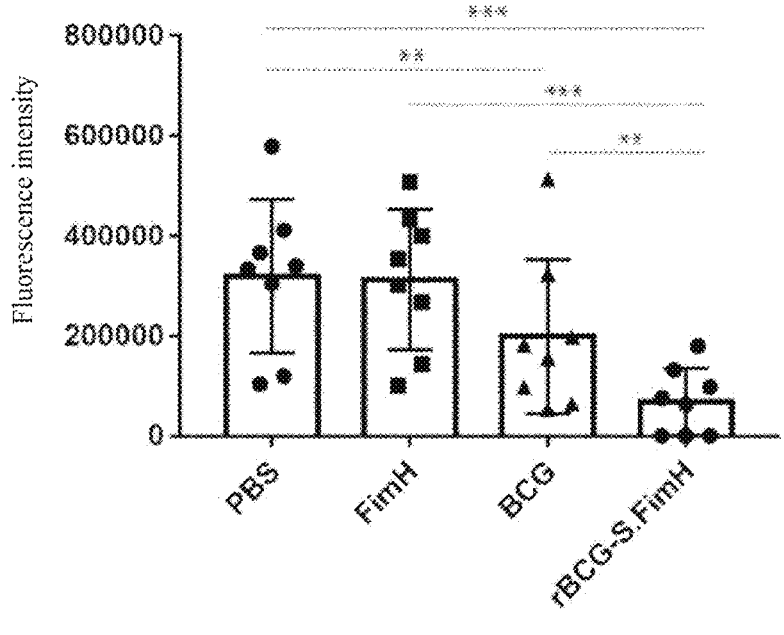
FIG. 8D is a histogram showing the comparison of quantification of in vivo fluorescence values in living imaging of mice.
Figure 8E:
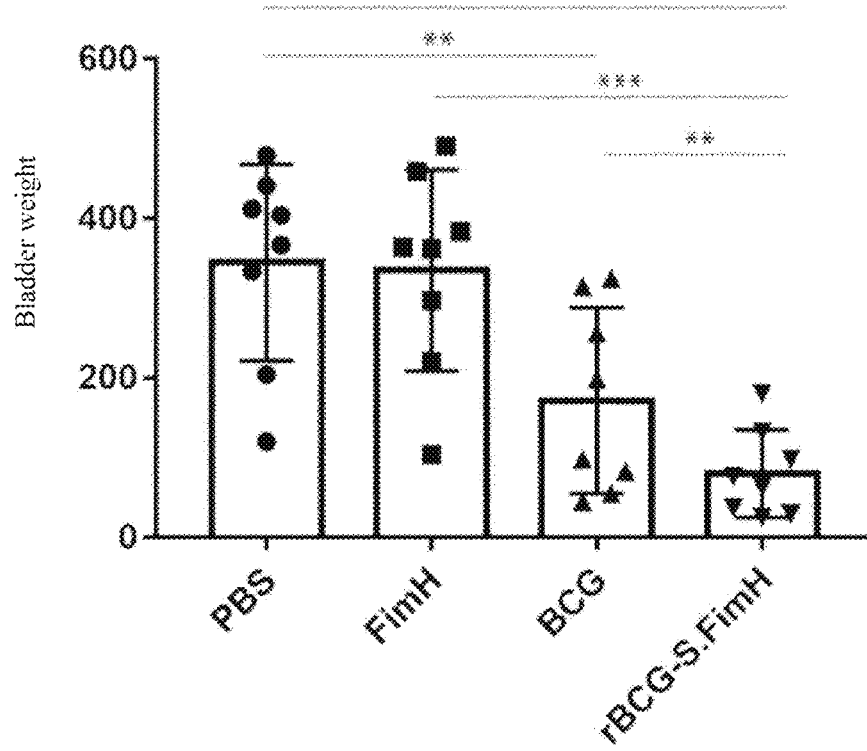
FIG. 8E is a histogram showing the comparison of the weights of mouse bladder tumors.

In the third week, the living imaging of mice in four groups was performed with IVSI. The living imaging of mice showed that rBCG-S.FimH significantly reduced the tumor size and tumor formation rate as compared with the BCG group, while the BCG group was significantly better than the FimH group, and the FimH group was similar to the PBS group, as shown in FIG. 8A. The mice in three groups were dissected, and their bladders were taken for pictures and weighed. FIG. 8B shows the comparison of tumor sizes (bladder sizes) in the mice in three groups, from which it can be seen that the treatment effect for tumor in rBCG-S.FimH group was extremely obvious, and the effect was significantly better than two other groups. FIG. 8C is the picture of mouse bladder after HE section. The results showed that in the rBCG-S.FimH group, there were 3 mice with normal bladder tissues and showing no tumors, thus the tumor-free rate was ⅜*100%=37.5%. The mice in the other three groups all had tumor tissues. Therefore, the rBCG-S.FimH group (37.5%) had a higher tumor-free rate than the BCG group (0%) and the FimH group (0%). FIG. 8D shows the quantification of in vivo fluorescence values in living imaging of mice. The weight in rBCG-S.FimH group was much lower than that in BCG group (p<0.01). The FimH group was basically the same as the control PBS group, and the bladder weight of the mouse in these two groups was much higher than that in the BCG group and, of course, more higher than that in the rBCG-S.FimH group. FIG. 8E shows that the bladder weight of the mouse in rBCG-S.FimH group was lower than that in the BCG group (p<0.01). The FimH group was basically the same as the control PBS group, and the BCG group was better than the FimH group. At the same time, references can be made to Table 3 to Table 4. In addition, C57/BL6 mice were instilled with BCG in the bladder, with 3 mice in each group. The experiment included control group, BCG group and recombinant BCG group. The fluorescence value of the bladder tissue after 4 hours of intravesical infusion with BCG (that is, the number of BCG that can adhere and internalize to the bladder tissue after 4 hours) was detected. The results showed that more BCG could adhere and internalize to the bladder of the mice in the recombinant BCG group, see Table 5.

The experimental results showed that there were significant differences between the BCG group and the FimH group with the recombinant BCG group (P<0.05).

TABLE 3

Fluorescence values in living imaging
of mouse bladder tumors in four groups

| | Control group | FimH group | BCG group | Recombinant BCG group |
|---|---|---|---|---|
| 1 | 579000 | 563000 | 515000 | 180000 |
| 2 | 412000 | 393000 | 325000 | 132000 |
| 3 | 341000 | 315000 | 156000 | 98000 |
| 4 | 304000 | 274000 | 198000 | 63000 |
| 5 | 367000 | 301000 | 98000 | 76000 |
| 6 | 334000 | 258000 | 183000 | 0 |
| 7 | 104000 | 102000 | 65000 | 0 |
| 8 | 120000 | 98000 | 55000 | 0 |

TABLE 4

Mouse bladder weights in 4 groups (unit: mg)

| | Control group | FimH group | BCG group | Recombinant BCG group |
|---|---|---|---|---|
| 1 | 479 | 475 | 315 | 180 |
| 2 | 412 | 406 | 325 | 132 |
| 3 | 441 | 431 | 256 | 98 |
| 4 | 404 | 389 | 198 | 63 |
| 5 | 367 | 338 | 98 | 76 |
| 6 | 334 | 301 | 83 | 37 |
| 7 | 204 | 121 | 45 | 25 |
| 8 | 120 | 99 | 55 | 29 |

TABLE 5

Fluorescence values of mouse bladder tissues in three groups
after 4 hours of intravesical instillation with BCG

| | Control group | BCG group | Recombinant BCG group |
|---|---|---|---|
| 1 | 363 | 2063 | 5958 |
| 2 | 241 | 1198 | 7012 |
| 3 | 402 | 2147 | 6213 |

In terms of tumor elimination, the tumor retention rate in the control group and the BCG group was 100%, and the elimination rate was 0%, while in the recombinant BCG group, only 62.5% of tumors were remained, that is, the complete elimination rate was 37.5%.

The instillation experiment of the mouse with orthotopic tumor implantation in bladder showed that the anti-tumor effect of rBCG-S.FimH was stronger than that of BCG. The bladder weight of mouse in the rBCG-S.FimH group was significantly lower than that in the BCG group, the FimH group and the PBS group, and the fluorescence intensity was significantly lower than that in the BCG group, the FimH group and the PBS group, and the tumor-free rate after treatment was higher than that in the BCG group, the FimH group and the PBS group. From Table 4, FIGS. 8A, 8C, 8D, and Tables 3-5, it can be clearly known that the anti-tumor effect in FimH group was lower than that in the BCG group, and was close to that in the PBS group. Therefore, in many experiments, the inventors focused on comparing rBCG-S.FimH with BCG whose effect is better. This is more meaningful.

Example 7

Figure 9A:
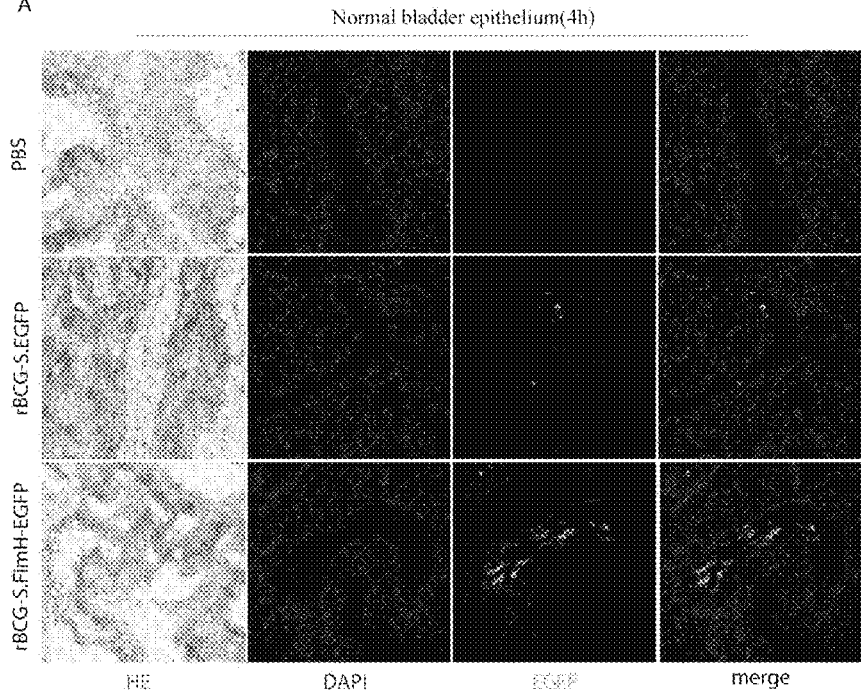
FIG. 9A is a graph showing the adhesion and internalization to normal epithelial cells of bladder in different groups.
Figure 9B:
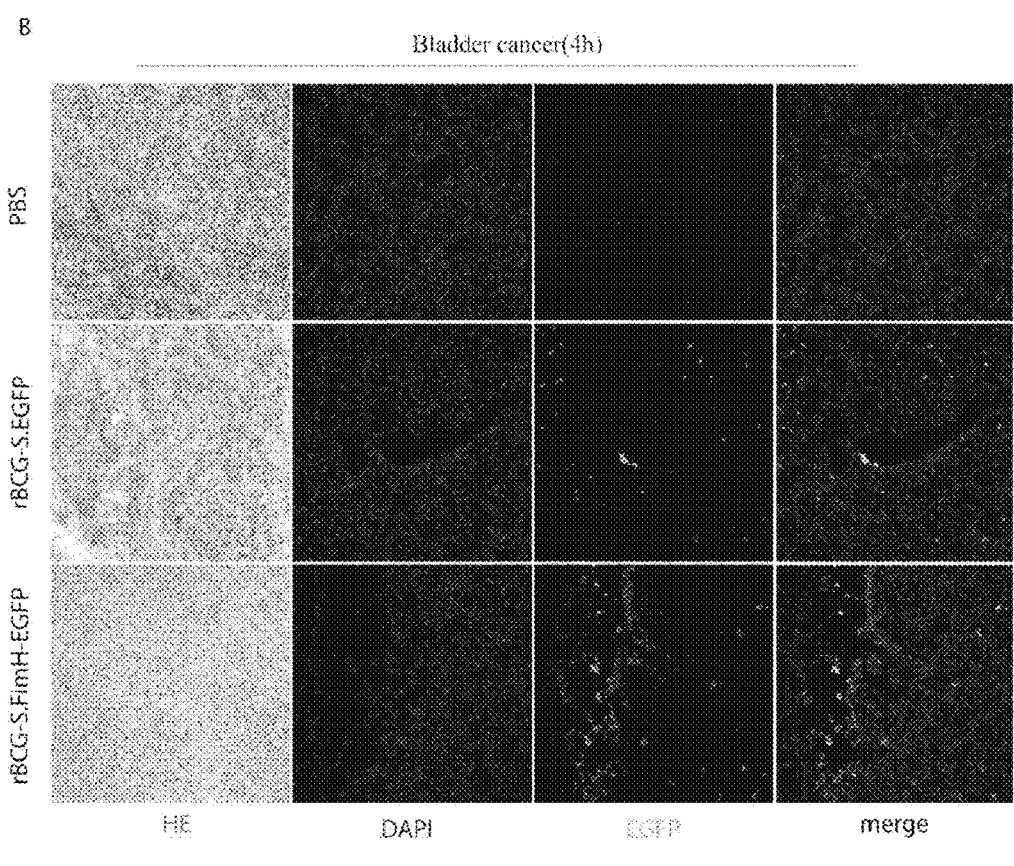
FIG. 9B is a graph showing the adhesion and internalization to bladder tumor cells in different groups.
Figures 9C, 9D:
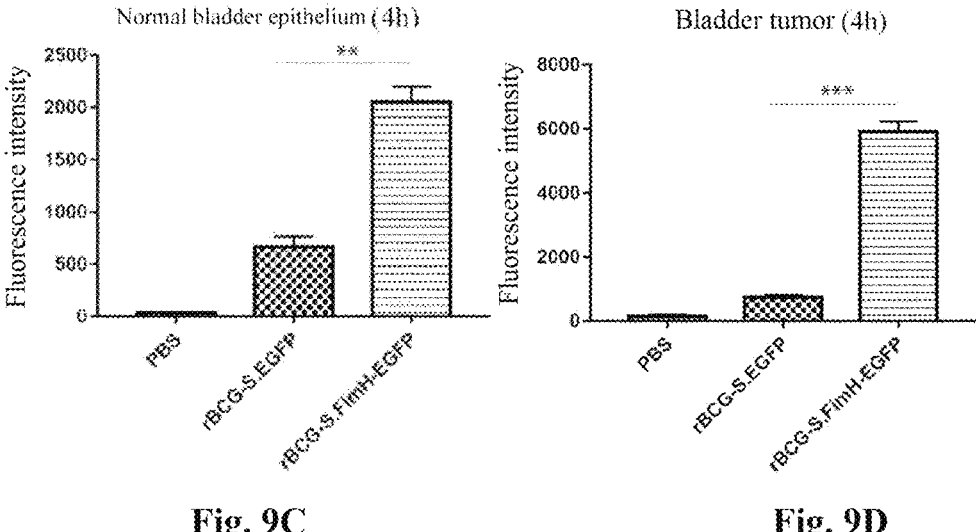
FIG. 9C is a graph showing the quantification of fluorescence of the adhesion and internalization to normal epithelial cells of bladder in different groups after 4 hours.
FIG. 9D is a graph showing the quantification of fluorescence of the adhesion and internalization to bladder tumors in different groups after 4 hours.
Figures 9E, 9F, 9G, 9H, 10A:
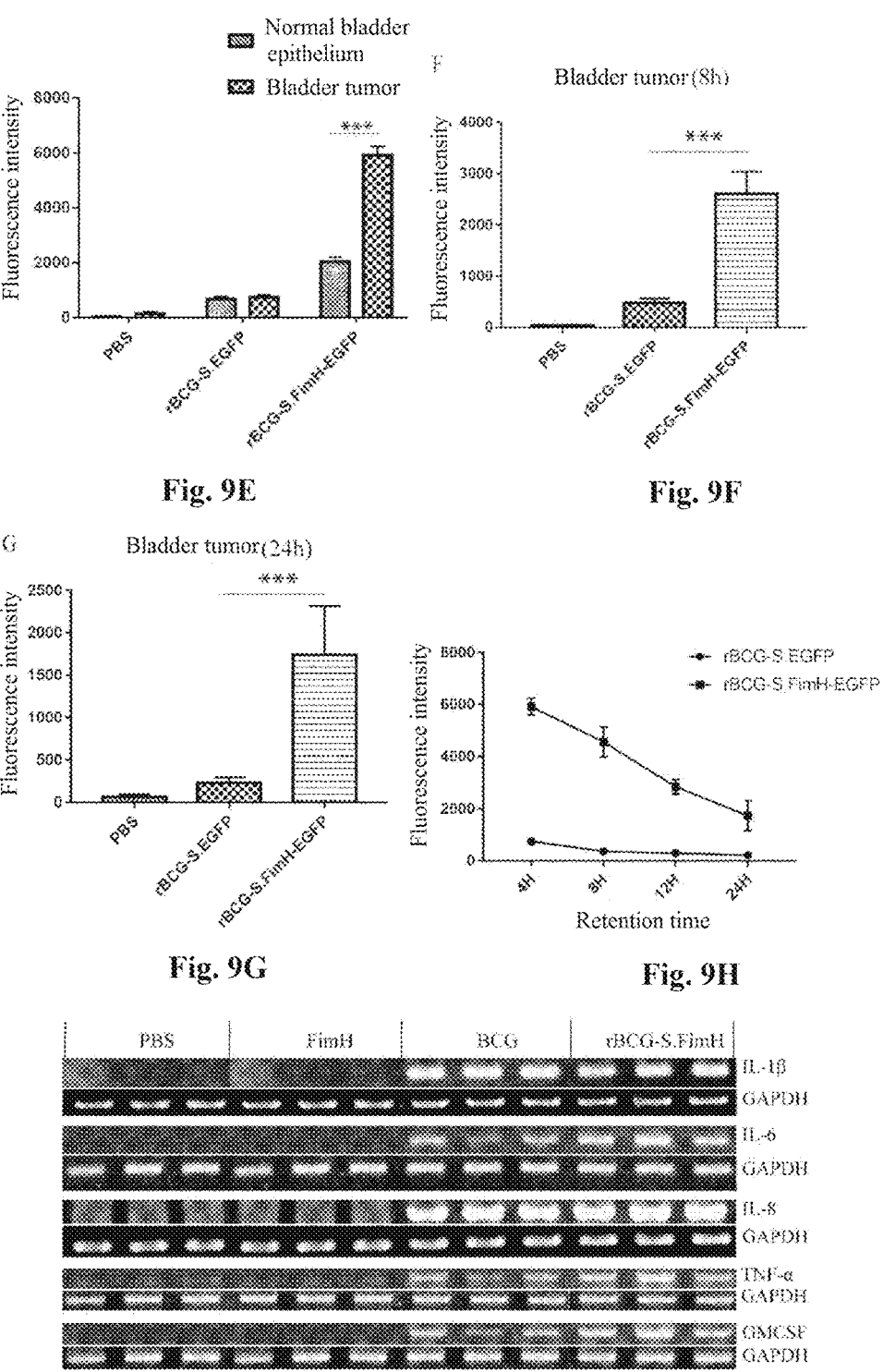
FIG. 9E is a graph showing the quantification of the propensities to adhere and internalize to bladder tumors in different groups after 4 hours.
FIG. 9F is a graph showing the quantification of the propensities to adhere and internalize to bladder tumors in different groups after 8 hours.
FIG. 9G is a graph showing the quantification of fluorescence value for the frozen slice of mouse bladder tumor after 24 hours.
FIG. 9H is a graph showing the quantification of the propensities to adhere and internalize to bladder tumors in different groups after different times.
FIG. 10A is a graph showing the expressions of cytokines in innate immune effects in different groups.

The mouse intravesical infusion experiment was performed to illustrate the high adhesion and internalization of the recombinant BCG rBCG-S.FimH-EGFP to bladder epithelial cells and the propensity to adhere and internalize to bladder tumor cells. After instillation, urination was done and then the bladder was taken out to make frozen slices, for which a confocal imaging was performed. FIG. 9 shows that rBCG-S.FimH has stronger adhesion to mouse bladder and has longer retention time. Specifically, for FIG. 9A, the bladders of mice were instilled with PBS, rBCG-S.EGFP and rBCG-S.FimH-EGFP respectively, 4 hours after which, the mice were dissected and their bladders were taken to make frozen slices. As a result, the rBCG-S.FimH-EGFP group had stronger adhesion and internalization to normal epithelial cells of bladder than the rBCG-S.EGFP group (p<0.01). For FIG. 9B, an orthotopic tumor implantation in mouse bladder was performed for one week, then the bladders of mice were instilled with PBS, rBCG-S.EGFP and rBCG-S.FimH-EGFP respectively, 4 hours after which, the mice were dissected and the bladder tumors were taken to make frozen slices. As a result, the rBCG-S.FimH-EGFP group had stronger ability to adhere and internalize to bladder tumor cells (p<0.01). FIG. 9C shows the quantification of fluorescence value for the frozen slice of normal mouse bladder after 4 hours. FIG. 9D shows the quantification of fluorescence value for the frozen slice of mouse bladder tumor after 4 hours, it can be seen from the figure that the fluorescence value in rBCG-S.FimH-EGFP group was far superior to the other two groups. FIG. 9E shows that compared with rBCG-S.EGFP, rBCG-S.FimH-EGFP has a stronger propensity to adhere and internalize to bladder tumors. FIG. 9F shows the quantification of fluorescence value for the frozen slice of mouse bladder tumor after 8 hours. FIG. 9G shows the quantification of fluorescence value for the frozen slice of mouse bladder tumor after 24 hours. FIG. 9H shows the quantification of fluorescence value for the frozen slice of mouse bladder tumor in the rBCG-S.EGFP group and rBCG-S.FimH-EGFP group after 4 hours, 8 hours, 12 hours and 24 hours. From which it can be seen that rBCG-S.FimH has stronger adhesion to mouse bladder and has longer retention time. In conclusion, it can also be clearly found from these histograms that rBCG-S.FimH-EGFP has stronger adhesion to bladder epithelial cells and tumor cells and has longer retention time.

Example 8

Figure 10B:
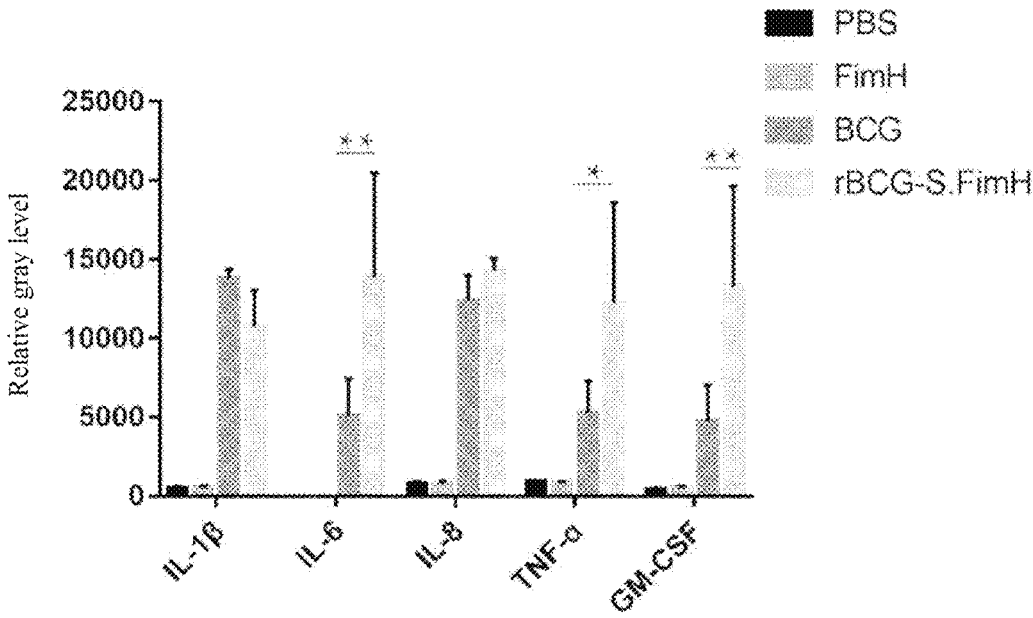
FIG. 10B shows the quantification of the results in FIG. 10A obtained by a gray level analysis.

The C57/BL6 mouse bladder orthotopic tumor implantation (MB49-Luc) model was used, and the mice were divided into 4 groups. The number of mice in each group was the same. The four groups were instilled with PBS, FimH, BCG, and rBCG-S.FimH respectively. Three weeks after which, the bladder tissues of mice were taken for RT-PCR experiments. The results showed that in the rBCG- S.FimH group, the expressions of cytokines IL-6, TNF-α and GM-CSF in innate immune effectors were significantly up-regulated, as compared with the other three groups (P<0.05). The expressions in the FimH group and the PBS group were much lower than that in the BCG group, and no obvious effect was observed. As shown in FIG. 10, FIG. 10A is a graph showing the expressions of cytokines in innate immune effects in different groups. FIG. 10B shows the quantification of the results in FIG. 10A obtained by gray level analysis (*P<0.05, **P<0.01).

In conclusion, through the experiments, it can be clearly confirmed that the recombinant BCG of the present application has the effect of enhancing the innate immune effect.

Example 9

Figure 11A:
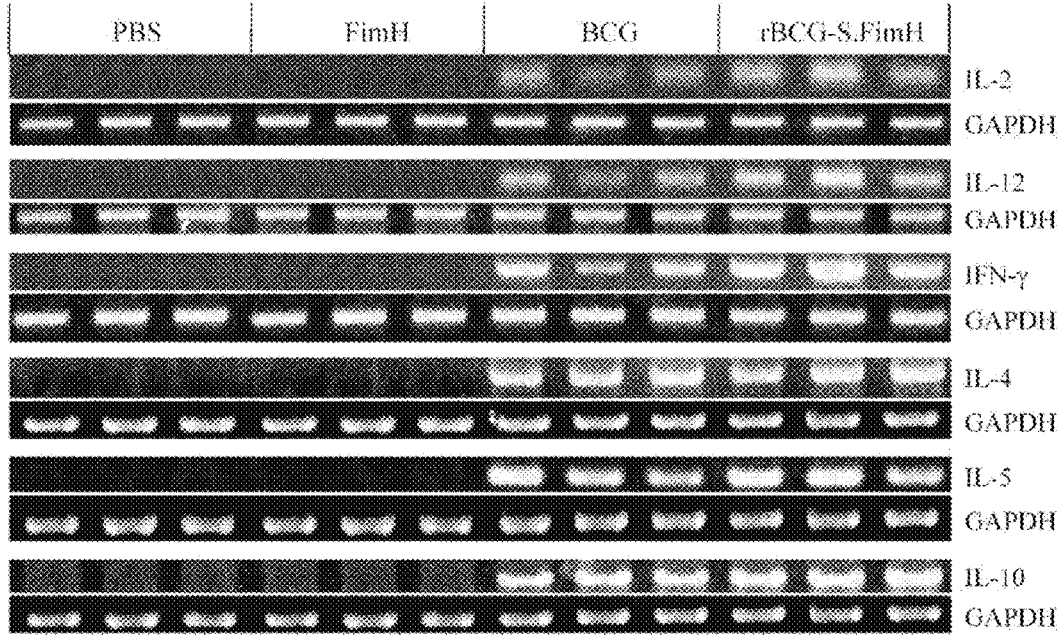
FIG. 11A is a graph showing that mouse intravesical instillation with rBCG-S.FimH enhances the adaptive immune effect as compared to the instillation with BCG, as detected by RT-PCR.
Figure 11B:
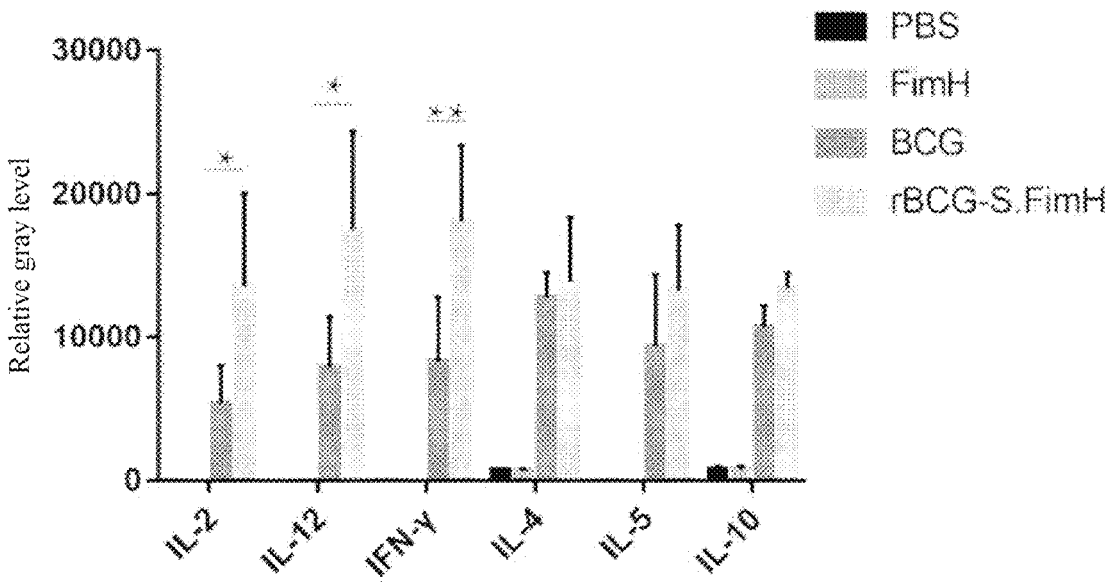
FIG. 11B shows the quantification of gray level analysis results for FIG. 11A.

The C57/BL6 mouse bladder orthotopic tumor implantation (MB49-Luc) model was used, and the mice were divided into 4 groups. The number of mice in each group was the same. The four groups were instilled with PBS, FimH, BCG, and rBCG-S.FimH respectively. Three weeks after which, the bladder tissues of mice were taken for RT-PCR assays. The results showed that in the rBCG-S.FimH group, the expressions of Th1 effector cytokines, IL-2, IL-12 and IFN-γ, were up-regulated, and this up-regulation was significantly higher than that in the BCG group, while in the PBS group and FimH group, no obvious effect was observed. FIG. 11A is a graph showing that mouse intravesical instillation with rBCG-S.FimH enhances the adaptive immune effect as compared to the instillation with BCG, as detected by RT-PCR. FIG. 11B shows the quantification of gray level analysis results for FIG. 11A (*P<0.05, **P<0.01).

In conclusion, through the experiments, it can be clearly confirmed that the recombinant BCG of the present application has the effect of enhancing the adaptive immune effect.

Example 10

Figure 12A:
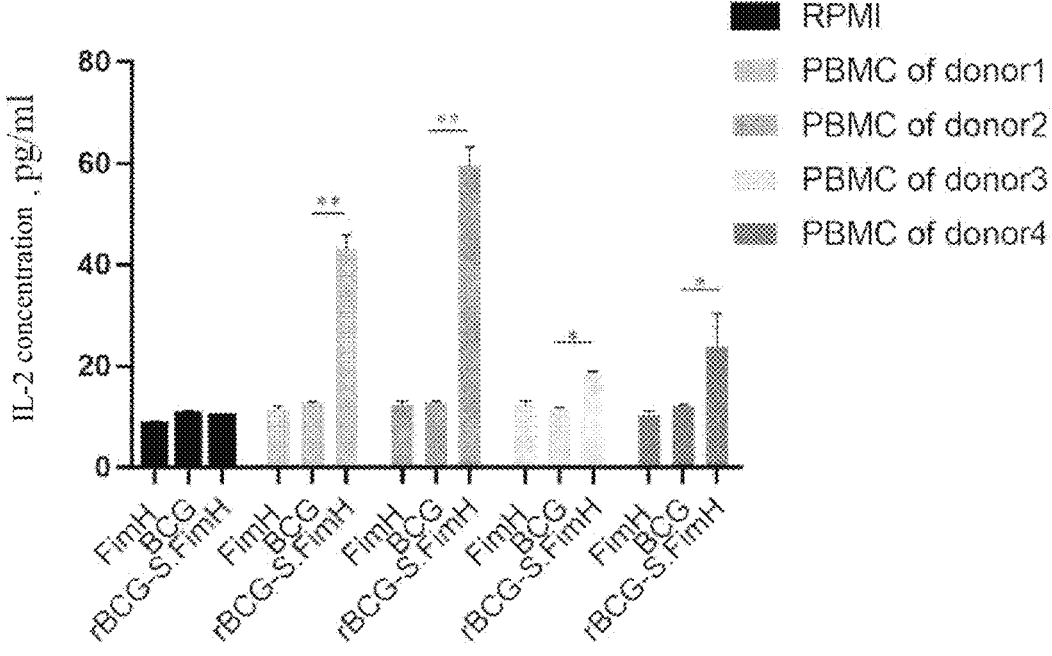
FIG. 12A is a graph showing the comparison of rBCG-S.FimH and BCG in enhancing the efficacy of human PBMC against bladder tumor cells and in the level of IL-2 secretion.
Figure 12B:
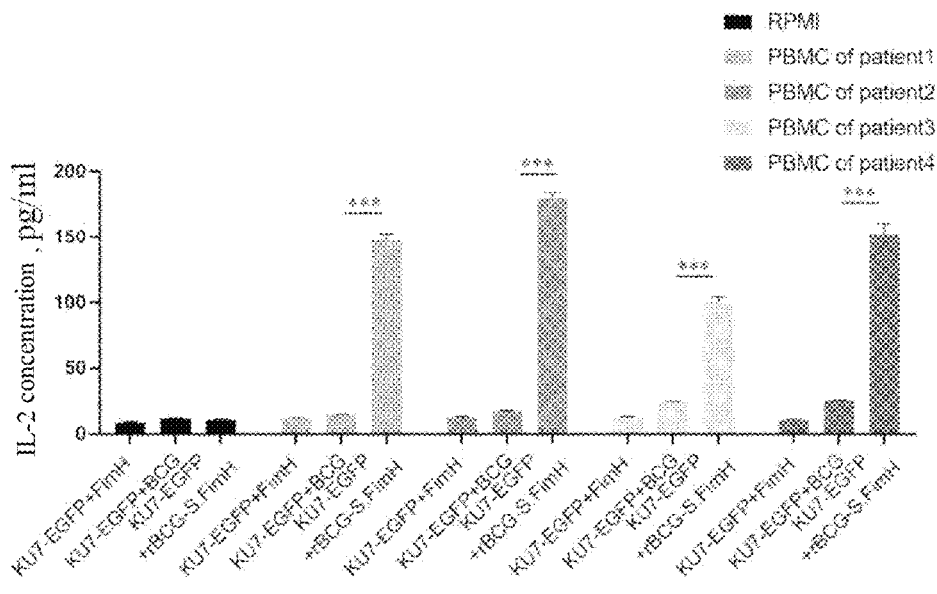
FIG. 12B is a graph comparing the ability of rBCG-S.FimH to stimulate PBMC to secrete IL-2.
Figure 12C:
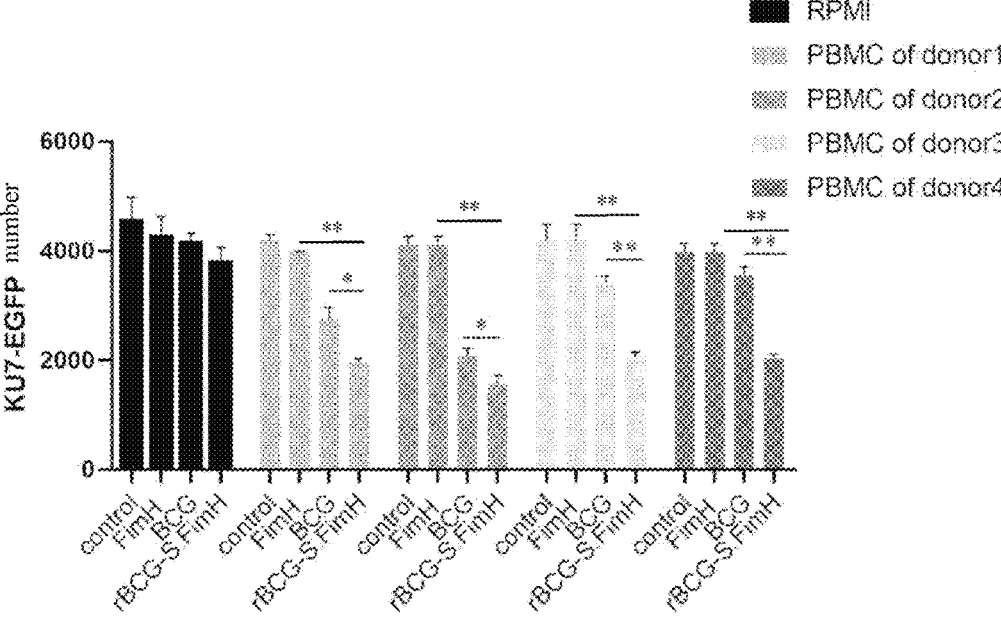
FIG. 12C is a graph showing the fluorescent microscopic counting of bladder tumor KU7-EGFP cells in each group in FIG. 12B.

As shown in FIG. 12, in order to confirm whether rBCG-S.FimH and BCG can enhance the efficacy of human PBMC against bladder tumor cells and the level of IL-2 secretion, multiple sets of experiments were performed. Specifically, for FIG. 12A, the peripheral blood PBMCs were extracted from 4 healthy volunteers, then co-incubated with BCG, FimH, and rBCG-S.FimH, respectively. 48 hours later, the supernatant was collected to detect the expression amount of IL-2 protein. As a result, the ability of rBCG-S.FimH to stimulate PBMC to produce IL-2 was stronger than that of BCG and FimH. For FIG. 12B, in each BCG group, the PBMCs were co-cultured with bladder tumor KU7-EGFP cells. 72 hours later, the supernatant was collected, and the concentration of IL-2 protein was detected by ELISA. It was found that bladder tumor KU7-EGFP cells further increased the ability of rBCG-S.FimH to stimulate PBMC to secrete IL-2. FIG. 12C is a graph showing the fluorescent microscopic counting of bladder tumor KU7-EGFP cells in each group in FIG. 12B (*P<0.05, **P<0.01).

In conclusion, through the experiments, it can be clearly confirmed that the recombinant BCG of the present application can enhance the efficacy of human PBMC against bladder tumor cells and the level of IL-2 secretion.

In the present invention, the recombinant BCG can achieve a synergistic effect through a variety of action modes or mechanisms, so that it has an excellent anti-bladder cancer effect. When FimH used alone, the effect of enhancing immunity is extremely low. In addition, FimH regulates immunity mainly in the process of anti-microbial infection, and the mechanism therein is different from that of the present invention, so that FimH has almost no anti-tumor effect. Therefore, the effect of FimH is much lower than that of BCG, whether in anti-tumor effect or in immune-enhancing effect. So, in the above-mentioned examples, the inventors focus on comparing the recombinant BCG with the BCG whose effect is higher than that of FimH, and the effects of the recombinant BCG in all aspects are significantly superior to that of BCG.

Although embodiments of the present invention have been shown and described, it will be understood by those of ordinary skill in the art that various changes, modifications, substitutions and alterations can be made in these embodiments without departing from the principles and spirit of the invention, and the scope of the invention is defined by the claims and their equivalents.

The invention claimed is:

1. A recombinant Bacille Calmette-Guérin (BCG), wherein the recombinant BCG is a BCG capable of expressing a FimH protein on its own surface, wherein the recombinant BCG is deposited at China General Microbiological Culture Collection Center with an accession number of 19540, and wherein the recombinant BCG, via the FimH protein expressed on its surface, specifically binds to subjects with FimH protein-binding properties.

2. A bladder tumor inhibitor, wherein the inhibitor is the recombinant BCG according to claim 1, and the recombinant BCG is capable of specifically binding to bladder cells to inhibit bladder tumors and is capable of enhancing the anti-tumor effect of peripheral blood mononuclear cells, thus achieving better treatment effects against bladder tumors comprehensively.

3. The recombinant BCG according to claim 1, wherein the recombinant BCG comprises a 19ss signal peptide and wherein a nucleotide sequence of a 19ss signal peptide-expressing gene is:

(SEQ ID No.: 1)
TATGAAGCGTGGACTGACGGTCGCGGTAGCCGGAGCCGCCATTCTG

GTCGCAGGTCTTTCCG.

4. A method of treating cancer in a subject in need thereof, comprising administering to the subject a therapeutically effective amount of the recombinant BCG according to claim 1, wherein the cancer is bladder cancer.

* * * * *